US00PP32981P2

(12) United States Plant Patent
Austin

(10) Patent No.: US PP32,981 P2
(45) Date of Patent: Apr. 20, 2021

(54) ***ROSA HYBRIDA* SHRUB PLANT NAMED 'AUSEGDON'**

(50) Latin Name: *Rosa hybrida*
Varietal Denomination: AUSegdon

(71) Applicant: David Austin Roses Ltd., Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 16/602,906

(22) Filed: Dec. 19, 2019

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./107
CPC ..... A01H 6/749; A01H 5/02
See application file for complete search history.

(56) References Cited

U.S. PATENT DOCUMENTS

PP17,500 P2 3/2007 Austin
PP31,400 P2 1/2020 Austin

*Primary Examiner* — Keith O. Robinson
(74) *Attorney, Agent, or Firm* — KPPB LLP

(57) ABSTRACT

An optical biomodule for detecting a disease specific biomarker(s), utilizing enhanced fluorescence emission (due to integration of a three-dimensional (3-D) protruded structure(s)) in a fluidic container/zero-mode waveguide, upon chemical binding of a disease specific biomarker(s) with its corresponding disease specific biomarker binder(s) is disclosed. The three-dimensional (3-D) protruded structure(s) can be coupled with a photonic crystal and/or a metamaterial and/or a metamaterial of Epsilon-Near-Zero (ENZ) of a suitable wavelength range. Furthermore, the enhanced fluorescence emission can be modulated by a synthetic Cas13 protein coupled with a CRISPR RNA (crRNA) and a quenched fluorescent reporter. Alternatively, a suitable synthetic substitute of a synthetic Cas13 protein coupled with a CRISPR RNA (crRNA) containing variable targeting sequence can also be utilized.

1 Drawing Sheet

Classification: The present invention relates to a new *Rosa hybrida* shrub of the market class 'English Rose'.

Variety denomination: The new plant has the varietal denomination 'AUSegdon'.

ORIGIN OF INVENTION

This invention relates to a new and distinct variety of shrub rose plant named 'AUSegdon', which was originated from the cross-pollination of the two 'unnamed' and unpatented seedlings of *Rosa hybrida*.

BACKGROUND OF THE INVENTION

The primary objective of this breeding was to produce a strong, vigorous rose shrub with bushy upright growth that bears a rose of soft, glowing apricot pink, each bloom packed with numerous delicately ruffled petals and held on a red-tinged stem where blooms begin as shallow cups, opening to full rosettes which reveal petals of a richer hue which gradually pale over time. The blooms have a strong fruity fragrance.

SUMMARY OF THE INVENTION

Among the features which distinguish the new variety from others presently available and commercial rose cultivars known to the inventor is the following combination of characteristics: a strong, vigorous shrub of bushy upright growth and good disease resistance bearing blooms the color of soft apricot pink, with many delicately-ruffled petals and red tinged stems where the blooms begin as shallow cups and open to full rosettes with a strong fruity fragrance.

Asexual reproduction of the new variety by budding as performed in Albrighton, Wolverhampton, United Kingdom, shows that the foregoing and other distinguishing characteristics come true to form and are established and transmitted through succeeding asexual propagations. 'AUSegdon' may be asexually propagated by budding. The budding successfully occurred on an unpatented plant/rootstock *Rosa dumetorum* 'Laxa' for the observed plants.

COMPARISON WITH PARENTS

The maternal and paternal parents of 'AUSegdon' are two unnamed seedlings. The new rose may be distinguished from its seed parent, by the following combination of characteristics: the seed parent is of a mauve color compared to the apricot pink of 'AUSegdon'. The new rose may be distinguished from its pollen parent, by the following combination of characteristics: the pollen parent has a paler pink bloom of a more incurved shape, and the plant has a larger broader growth compared to 'AUSegdon'.

COMPARISON WITH THE CLOSEST COMMERCIALLY AVAILABLE CULTIVAR

The closest commercially available cultivar to the new variety are 'AUSearnshaw' (U.S. Plant Pat. No. 31,400) and 'AUSrumba' (U.S. Plant Pat. No. 17,500). The blooms of 'AUSegdon' are RHS 65B (red-purple), whereas the blooms of 'AUSearnshaw' are RHS 36B (red group) with a yellow center (RHS 10C (yellow) and the blooms of 'AUSrumba' are RHS 50D (red group). 'AUSegdon' has a rosette bloom with ruffled petals, whereas the blooms of 'AUSearnshaw' are flat topped with a button eye, and the blooms of 'AUSrumba' are cupped with entire petals. The leaves of 'AUSegdon' are medium glossy, whereas the leaves of 'AUSearnshaw' are more glossy and the leaves of 'AUSrumba' are matt.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSegdon' specimens were made at a nursery in Albrighton, Wolverhampton, United Kingdom. The following description is of 1 year-old rose plants of the new variety grown in a garden environment in Albrighton, Britain in the month of July. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size.*—About 2.2 cm long and 1.7 cm in diameter when the petals start to unfurl.

*Form.*—The bud form is pointed ovoid and broad based.

*Color.*—When sepals first divide, the bud color is RHS 60D (red-purple group). When half blown, the upper sides of the petals are RHS 65B (red-purple group) (top half) and RHS 14C (yellow-orange group) (middle), and the lower sides of the petals RHS 65B (red-purple group)(top half) and RHS 14C (yellow-orange group)(middle).

*Calyx.*—Shape: star shape, with the sepals folding back against the stems. Length: 5 cm. Diameter: 5 cm.

*Sepals.*—Arrangement: Regularly arranged. Color: Upper Surface: RHS 147D (yellow-green group). Lower Surface: RHS 147C (yellow-green group) with some RHS 71B (red-purple group). Length: 2 cm. Width: 9 mm. Shape: Lanceolate. Surface texture: Upper Surface: Downy. Lower Surface: Downy. Number: There are 3 lightly appendaged sepals, and 2 unappendaged sepals with hairy edges. Sepal Extensions: Weak.

*Receptacles.*—Color: RHS 144B (yellow-green group). Shape: Funnel. Size: Medium, about 1 cm long×9 mm wide. Surface: Smooth.

*Peduncle.*—Length: Short, averaging about 6 cm. Surface: Smooth. Color: RHS 144B (yellow-green group). Strength: Strong.

Blooms:

*Size.*—Large, average open diameter is about 9 cm.

*Borne.*—Several together approximately 4-14 blooms having a rounded shape.

*Stems.*—Strength: Strong, average length is about 6 cm. Diameter: 3 mm.

*Form.*—When first open, bloom is cupped. Permanence of bloom: outer petals curl back.

*Profile.*—The lower profile of the bloom is concave.

*Flower type.*—Double.

Petalage: Number of petals under normal conditions: 90.

*Color.*—The upper sides of the petals are RHS 65C (red-purple group). The reverse sides of the petals are RHS 65C (red-purple group). The base of the petals has a yellow spot RHS 3B (yellow group). The size of the yellow spot is large.

*Variegations.*—None.

*Discoloration.*—The general tonality at the end of the first day is RHS 65B (red-purple group), and at the end of the third day is RHS 65C (red-purple group).

*Fragrance.*—Strong. Character of fragrance: Fruity.

Petals:

*Texture.*—Satiny.

*Size.*—Width: 1.7 mm-2 mm. Length: 3 cm.

*Surface.*—Smooth.

*Shape.*—Obovate.

*Margin.*—Ruffled.

*Apex shape.*—Rounded.

*Base shape.*—Acute.

*Form.*—Incurved.

*Arrangement.*—Regular.

*Petaloids.*—Number: Few (approx. 10-13). Color: RHS 49A (red group). Length: 0.6-1.5 cm. Width: 0.4-1 cm. Shape: Obovate. Margin: Entire.

*Persistence.*—Petals drop off cleanly before drying.

*Lastingness.*—On the plant: Short about 4 days. As a cut flower: not tested.

Reproductive parts:

*Stamens.*—Number: approximately 20. Length: 5 mm.

*Anthers.*—Length: 2.5 mm. Color: RHS 14C (yellow-orange group). Arrangement: Mixed with petaloids.

*Filaments.*—Color: RHS 14C (yellow-orange group). Length: 5 mm.

*Pollen.*—Color: RHS 17A (yellow-orange group). Amount: Scarce.

*Pistils.*—Number: Approximately 40. Length: 9-11 mm.

*Styles.*—Color: Mostly RHS 155A (white group) with RHS 63B (red-purple group) just beneath the stigma. Length: 8 mm.

*Stigmas.*—Color: RHS 14B (yellow-orange group). Length: 1 mm.

*Hips.*—NONE Observed.

PLANT CHARACTERISTICS

Plant form: Shrub.

Plant growth: Vigorous, upright and bushy.

Age to maturity: 2 years.

Mature plant: Height: 120 cm. Width: 90 cm.

Rootstock: *Rosa dumetorum* 'Laxa' for the observed plants.

Foliage:

*Number.*—Leaflets on normal mid-stem leaves is: 5 (including terminal leaflet).

*Size.*—Large, about 15 cm long×11 cm wide.

*Quantity.*—Abundant. Number of leaves per flowering stem is: approx. 13.

*Color.*—New foliage: Upper side: RHS 146B (yellow-green group). Lower side: 191B (grayed-green group) tinged with RHS 182A (grayed-red group). Old foliage: Upper side: RHS 147A (yellow-green group). Lower side: RHS 146B (yellow-green group).

Leaflets:

*Size.*—About 6 cm long×5 cm wide.

*Shape.*—Pointed oval.

*Base shape.*—Cordate.

*Apex shape.*—Acuminate.

*Texture.*—Leathery.

*Glossiness.*—Medium.

*Edge.*—Serrated.

*Undulation of margin.*—Medium.

*Serrations.*—Single.

*Petiole.*—Color: RHS 146B (yellow-green group). Length: 4 cm. Width: 2 mm. Surface Texture: Glandular.

*Petiole rachis.*—Color: RHS 146B (yellow-green group). Underside: with prickles.

*Stipules.*—Length: 1.5 cm, smooth. Color: RHS 146B (yellow-green group).

*Auricle.*—Shape: Lanceolate. Length: 5 mm. Width: 3 mm. Color: RHS 146B (yellow-green group).

*Vein color.*—Color: RHS 146B (yellow-green group).

*Venation pattern.*—Reticulate.

Wood:

*New wood.*—Color: RHS 182A (grayed-red group). Bark: Smooth.

*Old wood.*—Color: RHS 146B (yellow-green group). Bark: Smooth.

Branching habit:

*Number.*—3.

*Dimensions.*—Length: 80 cm. Diameter: 7 mm.

Stems:

*Mature stem.*—Length: 100 cm. Diameter: 7 mm.

*Internode distance.*—4 cm. The above measurements are all variable, depending on growing conditions in a season.

*Stem pubescence present.*—No.

Prickles:

*Quantity.*—On main canes from base: Ordinary. Number per stem length: 13 per 10 cm. On laterals from main canes: Ordinary. Number per stem length: 13 per 10 cm.

*Form.*—Deep concave.

*Length.*—5 mm.

*Color when young.*—RHS 60C (red-purple group).

*Color when mature.*—RHS 60B (red-purple group).

Small prickles:

*Quantity.*—Main stalk: Few. Number per stem length 2 per 10 cm. Laterals: Few. Number per stem length 2 per 10 cm.

*Color.*—When young: RHS 60B (red-purple group). When mature: RHS 60B (red-purple group).

Disease resistance:

*Powdery mildew* (*Podosphaera pannosa*).—Resistant.

*Downy mildew* (*Peronospora species*).—Moderately resistant.

*Blackspot* (*Diplocarpon rosae*).—Resistant.

*Rust* (*Phragmidium tuberculatum*).—Resistant.

Pest Resistance: Not tested.

Winter Hardiness: Not tested.

Growing conditions: Normal garden conditions.

What is claimed is:

1. A new and distinct variety of rose plant of the shrub class, substantially as herein shown and described.

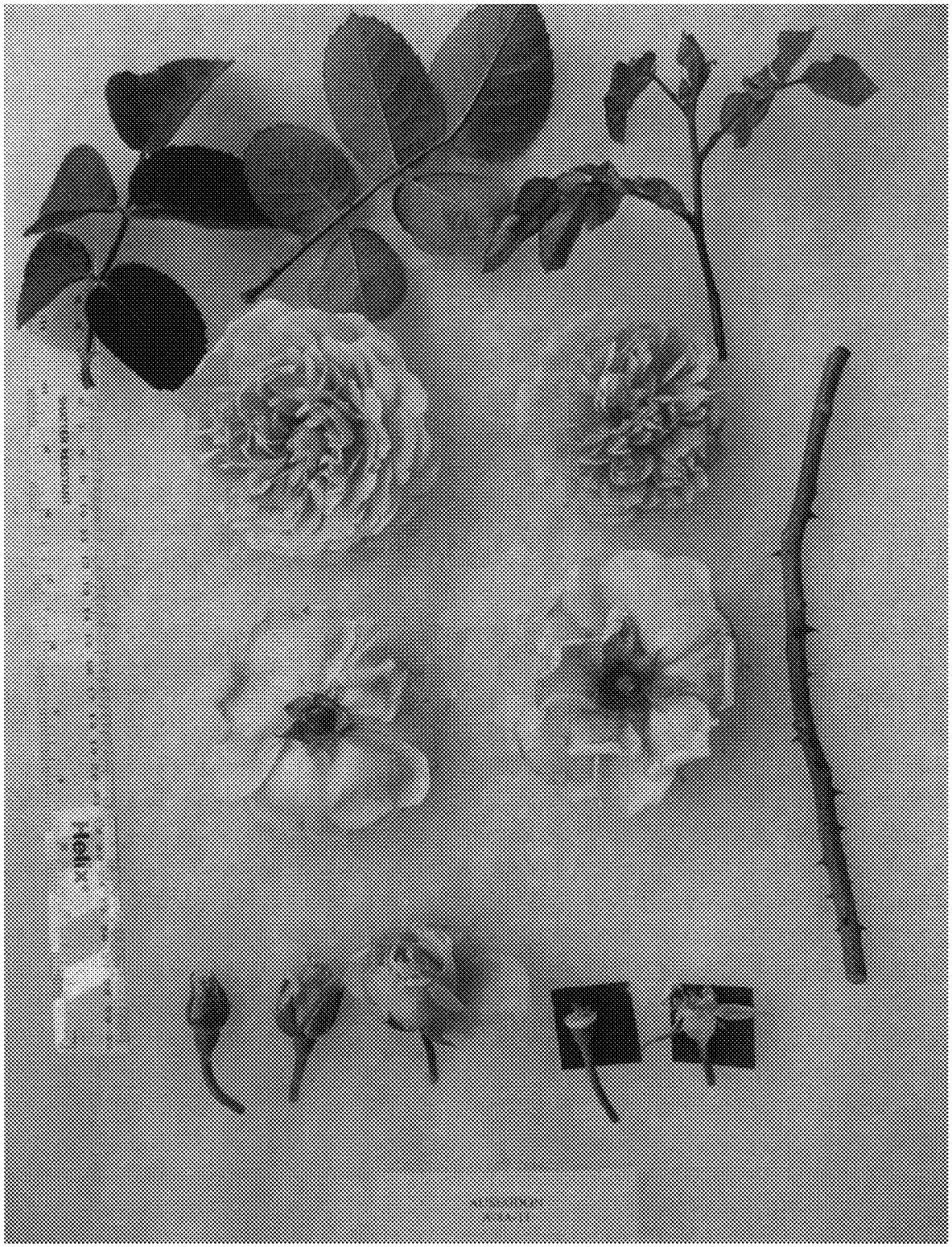

* * * * *